United States Patent [19]

Nash et al.

[11] 4,355,183

[45] Oct. 19, 1982

[54] DECOLORIZATION TREATMENT

[75] Inventors: Martin E. Nash; Edward E. Huxley, both of Borger, Tex.

[73] Assignee: Phillips Petroleum Company, Bartlesville, Okla.

[21] Appl. No.: 64,967

[22] Filed: Aug. 8, 1979

[51] Int. Cl.³ .......................................... C07C 149/18
[52] U.S. Cl. ...................... 568/19; 260/399; 560/2; 560/4; 562/512; 562/594; 562/597; 568/21; 568/62
[58] Field of Search .............. 260/609 C, 399; 568/62, 568/21; 562/597, 512, 594; 560/2, 4

[56] References Cited

U.S. PATENT DOCUMENTS

| | | | |
|---|---|---|---|
| 2,443,835 | 6/1948 | Pedersen | 568/19 |
| 2,793,190 | 5/1957 | Streicher | 562/597 |
| 3,004,048 | 10/1961 | Copenhaver et al. | 260/398.5 |
| 3,278,574 | 10/1966 | Louthan | 260/465.1 |
| 3,310,541 | 3/1967 | Breuers et al. | 260/82.1 |
| 3,730,339 | 5/1973 | Warner | 568/19 |

OTHER PUBLICATIONS

Kirk-Othmer, Encyclopedia of Chem. Technology, vol. 14, (1967) pp. 356-357, 366-367.
L. Miall et al., A New Dictionary of Chemistry, pp. 427-428, Wiley and Sons, (1968).
A. Laudere et al., Chem. Abst. 70:100508k (1969).
E. Eberius, Chem. Abst. 70:40119x (1969).

*Primary Examiner*—Donald G. Daus
*Assistant Examiner*—M. C. Eakin
*Attorney, Agent, or Firm*—H. D. Doescher

[57] ABSTRACT

Inhibition of the formation of color bodies and color-forming materials and other contaminants and/or decolorization of discolored sulfur-containing organic compounds containing divalent sulfur by addition of a small amount of oxalic acid.

7 Claims, No Drawings

DECOLORIZATION TREATMENT

This invention relates to the inhibition and decolorization of sulfur-containing organic compounds. In accordance with another aspect, this invention relates to a method of decolorizing discolored sulfur-containing organic compounds containing divalent sulfur by treatment with oxalic acid. In accordance with another aspect, this invention relates to a method of inhibiting the formation of color bodies and color-forming materials and other contaminants, e.g., peroxides in sulfur-containing organic compounds by addition of oxalic acid. In accordance with a further aspect, this invention relates to color inhibited compositions comprising sulfur-containing organic compounds containing divalent sulfur and a small effective decolorizing amount of oxalic acid.

Sulfur-containing organic compounds frequently become discolored during the manufacture thereof or in subsequent purification procedures. The color-producing bodies generally result from the presence of transition metal ions or compounds. Such contaminants are occasionally added purposely, for example, as catalysts in the upstream operations, but are generally added inadvertantly by contact of the reaction mixture with steel containers, reactors, pipes, stirrers, etc. Such discoloration is frequently a reason for rejecting an entire batch of product, even though the contaminants may not be present in sufficiently large amount to influence downstream operations. Sulfur-chemical manufacturers are well aware of this problem and frequently employ all glass-lined equipment in order to avoid contact of the reaction mixture with steel, and also recommend to customers that downstream operations be conducted in glass-lined equipment.

This invention provides a means of decolorizing discolored organic materials for use in situations where the chemical effect of the contaminant or reaction products thereof are not critical. Thus, the nature of the color bodies is changed to non-color forming bodies, but they are not removed from the solution. Thus, this invention is not intended to cover situations in which the concentration of the metal contaminants must be reduced in order for the product stream to be compatible with downstream operations.

The transition elements most frequently encountered in discolored sulfur-containing compounds are iron and nickel, particularly iron. Other transition elements such as chromium, cobalt, molybdenum, etc., are also occasionally encountered. These contaminants are generally present in the reaction stream in amounts ranging up to 10 parts per million, though much larger amounts are occasionally encountered.

The color-forming contaminants in the sulfur-containing compounds are generally activated by contact with oxygen, particularly from air. It is within the scope of this invention, however, to treat discolored sulfur-containing compounds containing trace amounts of transition metals regardless of the conditions under which the color-forming species are activated.

Accordingly, an object of this invention is to provide a method for decolorizing discolored sulfur-containing organic compounds.

Another object of this invention is to provide a method of inhibiting the formation of color bodies and other color-forming materials and other contaminants in sulfur-containing organic compounds.

A further object of this invention is to provide a novel agent for inhibiting and decolorizing sulfur-containing organic compounds.

Other objects, aspects, as well as the several advantages of the invention will be apparent to those skilled in the art upon reading the specification and the appended claims.

In accordance with the invention, sulfur-containing organic compounds having divalent sulfur are contacted with a small amount of oxalic acid to inhibit the formation of color bodies and color-forming materials and decolorize discolored sulfur-containing compounds.

In accordance with one embodiment, the process is provided for decolorizing discolored sulfur-containing organic compounds by contacting the discolored compounds with a small, but effective, decolorizing amount of oxalic acid.

In accordance with another embodiment of the invention, a method is provided for inhibiting the formation of color bodies and color-forming materials and other contaminants, e.g., peroxides, in organic compounds containing divalent sulfur by the addition of oxalic acid.

A further embodiment of the invention comprises color inhibited compositions of sulfur-containing organic compounds containing divalent sulfur and oxalic acid.

The sulfur-containing organic compounds which are particularly susceptible to discoloration when trace amounts of transition metals are present include organic compounds having divalent sulfur containing carbon, hydrogen, and optionally, oxygen. Representative sulfur-containing organic compounds that can be used include mercaptans, sulfides, disulfides, mercaptoalcohols, alkylthioalcohols, mercaptocarboxylic acids, thiodicarboxylic acids, dithiodicarboxylic acids, mercaptocarboxylic esters, thiodicarboxylic esters, dithiodicarboxylic esters, and the like. The hydrocarbon portions of these compounds can be aliphatic, cycloaliphatic, or aromatic and generally contain from 2 to about 30 carbon atoms per molecule, preferably from 2 to about 12 carbon atoms per molecule.

Specific examples of sulfur-containing compounds which are within the scope of this invention include ethyl mercaptan, n-butyl mercaptan, t-butyl mercaptan, n-hexyl mercaptan, t-dodecyl mercaptan, n-octadecyl mercaptan, cyclohexyl mercaptan, 2-mercaptoethanol, 5-mercaptohexan-1-ol, 2-(ethylthio)ethanol, dimethyl sulfide, di-n-octyl sulfide, ditetradecyl sulfide, dimethyl disulfide, di-n-hexyl disulfide, 2-mercaptoacetic acid, 2-mercaptopropionic acid, 3-mercaptopropionic acid, 3,3'-thiodipropionic acid, 3,3'-dithiodipropionic acid, methyl 3-mercaptopropionate, dilauryl thiodiacetate, dimethyl 6,6'-dithiodioctanoate, and the like.

The amount of oxalic acid employed to decolorize the discolored sulfur-containing compound will vary widely depending upon the amount of color-forming bodies present in the solution. The amount of oxalic acid employed is a small but effective decolorizing and/or inhibiting amount which will be sufficient to decolorize the discolored sulfur-containing compound and/or inhibit the formation of color bodies and color-forming materials and other contaminants, e.g., peroxides. Generally, from about 1 part per million to about 0.5 weight percent based on total sulfur-containing compound will be adequate to decolorize the material. In most cases, and hence preferably, from about 10 to about 1,000 parts per million of oxalic acid will be employed to decolorize the sulfur-containing materials.

The reaction conditions under which the decolorization occurs can vary over a broad range, depending, of course, on the reactivity of the color-forming bodies present in the material. The decolorization will generally occur in the temperature range of about 0° to 100° C., and preferably from about 20° to 40° C. for whatever period of time is required for the decolorization to occur. The decolorization generally occurs very rapidly. Consequently, treatment for a time of from about 10 seconds to about 24 hours, and preferably from about 30 seconds to about 15 minutes is suitable.

An additional advantage to the present invention is the fact that reaction products of oxalic acid are carbon dioxide and water. Therefore, additional undesirable contaminants are not added to the sulfur-containing material by the introduction of oxalic acid to decolorize the material.

A further advantage to this invention lies in the costly and time-consuming alternatives available for the decolorization of the sulfur-containing material. Fractional distillation, solvent extraction, ion exchange, and the like can be employed to accomplish the decolorization, but the present invention is very rapid and inexpensive.

EXAMPLE

The following run illustrates the utility of this invention in decolorizing an unacceptably discolored batch of 2-mercaptoethanol.

To about 1 liter of pinkish-colored 2-mercaptoethanol containing approximately 5 ppm iron in a glass reactor was added approximately 0.1 gram oxalic acid. Agitation of the resulting solution for several minutes at room temperature resulted in a water-white solution. This, the undesirably discolored 2-mercaptoethanol was converted to an acceptable water-white color by treatment with a very small amount of oxalic acid according to the teaching of this invention.

We claim:

1. A process for decolorizing discolored sulfur-containing organic compounds having divalent sulfur and consisting essentially of sulfur, carbon, hydrogen, and, optionally, oxygen wherein the hydrocarbon portion of these compounds can be aliphatic, cycoaliphatic, or aromatic containing from 2 to about 30 carbon atoms per molecule which comprises contacting said discolored sulfur-containing compound with a small effective decolorizing amount of oxalic acid under conditions and for a period of time sufficient to decolorize said compounds.

2. A process according to claim 1 wherein the amount of oxalic acid present ranges from about 1 ppm to about 0.5 weight percent of the sulfur-containing organic compound and said organic compound is selected from the group consisting essentially of mercaptans, sulfides, disulfides, mercaptoalcohols, alkylthioalcohols, mercaptocarboxylic acids, thiodicarboxylic acids, dithiodicarboxylic acids, mercaptocarboxylic esters, thiodicarboxylic esters, and dithiodicarboxylic esters.

3. A process according to claim 1 wherein the amount of oxalic acid present ranges from about 10 to about 1000 ppm.

4. A process according to claim 1 wherein said sulfur-containing organic compound is a mercaptoalcohol.

5. A process according to claim 4 wherein said alcohol is 2-mercaptoethanol.

6. A method according to claim 1 wherein said contacting temperature is in the range of about 0° to 100° C.

7. A method according to claim 1 wherein pinkish-colored 2-mercaptoethanol containing iron is contacted with oxalic acid for a period of time sufficient to form a water-white solution.

* * * * *